US00PP33128P2

(12) United States Plant Patent
Losert

(10) Patent No.: US PP33,128 P2
(45) Date of Patent: Jun. 1, 2021

(54) ***CALIBRACHOA* PLANT NAMED 'KLECA19545'**

(50) Latin Name: ***Calibrachoa* sp.**
Varietal Denomination: KLECA19545

(71) Applicant: Klemm+Sohn GmbH & Co. KG, Stuttgart (DE)

(72) Inventor: Dominik Losert, Aspach (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/871,018

(22) Filed: May 10, 2020

(51) Int. Cl.
*A01H 5/02* (2018.01)
*A01H 6/82* (2018.01)

(52) U.S. Cl.
USPC ..... Plt./413
CPC ..... *A01H 6/821* (2018.05)

(58) Field of Classification Search
USPC ..... Plt./413
CPC ..... A01H 6/821; A01H 5/02
See application file for complete search history.

*Primary Examiner* — Keith O. Robinson
(74) *Attorney, Agent, or Firm* — Weatherly IP Solutions, LLC; Barbara Campbell

(57) ABSTRACT

A new *Calibrachoa* plant designated 'KLECA19545' particularly distinguished by orange-reddish flowers and a semi-upright habit, is disclosed.

1 Drawing Sheet

Genus and species: *Calibrachoa* sp.
Variety denomination: 'KLECA19545'.

BACKGROUND OF THE NEW PLANT

The present invention comprises a new and distinct variety of *Calibrachoa*, botanically known as *Calibrachoa* sp., and hereinafter referred to by the variety name 'KLECA19545'. 'KLECA19545' originated from a controlled cross in August 2016 in Stuttgart, Germany between the proprietary female *Calibrachoa* parent 'CA-2015-6388', (unpatented) and the proprietary male *Calibrachoa* 'KLECA17003', (unpatented). Progeny from the cross were planted and a single plant was selected in May 2017 in Stuttgart, Germany.

'KLECA19545' has been found to reproduce true to type in successive generations of asexual propagation in Stuttgart, Germany via vegetative tip cuttings.

SUMMARY

The following are the most outstanding and distinguishing characteristics of 'KLECA19545' when grown under normal horticultural practices in Stuttgart, Germany.

1. Orange-reddish flowers; and
2. A semi-upright plant habit.

DESCRIPTION OF THE PHOTOGRAPH

This new *Calibrachoa* plant is illustrated by the accompanying photograph of a plant grown outdoors in Stuttgart, Germany. The photograph shows the whole plant, including the flowers and foliage and buds. The colors shown are as true as can be reasonably obtained by conventional photographic procedures. The photograph is of a plant that is 14-weeks-old, taken outdoors on Jun. 4, 2019 in Stuttgart, Germany.

DESCRIPTION OF THE NEW VARIETY

The following detailed descriptions set forth the distinctive characteristics of 'KLECA19545'. The data which define these characteristics were collected from asexual reproductions carried out in Stuttgart, Germany. Data was collected on plants grown 18-weeks since potting in a greenhouse with no pinching or growth regulators. Color references are to The R.H.S. Colour Chart of The Royal Horticultural Society of London (R.H.S.), 5$^{th}$ edition (2007).

Classification:
- *Family*.—Solanaceae.
- *Botanical*.—*Calibrachoa* sp.
- *Designation*.—'KLECA19545'.

Parentage:
- *Female parent*.—'CA-2015-6388' (unpatented).
- *Male parent*.—'KLECA17003' (unpatented).

Plant:
- *Life cycle*.—Annual.
- *Form*.—Short-lived subshrub.
- *Habit*.—Semi-upright.
- *Height (from soil line to top of foliage)*.—13.6 cm.
- *Spread*.—31.0 cm.
- *Propagation type*.—Vegetative tip cuttings.
- *Time to produce a rooted cutting*.—3 weeks.
- *Pests and disease resistance*.—The new variety has not been observed to be resistant to pathogens and pests common to *Calibrachoa* plants.

Stems:
- *Stem color*.—RHS 144B (Yellow-Green).
- *Pubescence*.—Present.
- *Pubescence color*.—RHS 155A (White).
- *Stem diameter*.—0.25 cm.
- *Stem length*.—From soil line to first node: 2.5 cm. Total length: 20.5 cm.
- *Internode length*.—0.5 cm.

Foliage:
- *Arrangement*.—Alternate.
- *Shape*.—Lanceolate.
- *Apex*.—Obtuse.
- *Base*.—Attenuate.
- *Margin*.—Ciliate.
- *Variegation*.—Absent.

*Surface texture* (*both upper and lower surfaces*).—Pubescence present; puberulent.
*Pubescence color*.—RHS 155A (White).
*Venation*.—Arcuate.
*Venation color*.—Upper surface: RHS 137C (Green). Lower surface: RHS 1439D (Green).
*Length*.—2.1 cm to 3.9 cm.
*Width*.—0.9 cm to 1.5 cm.
*Color*.—Upper surface: RHS 137B (Green). Lower surface: RHS 147B (Yellow-Green).
*Fragrance*.—Absent.
*Petiole*.—Absent; sessile.

Inflorescence:
*Flowering type*.—Single flowers.
*Flowering requirements*.—A minimum of light sun is required.
*Flowering season*.—Continuous flowering from spring through autumn and all the time/year around in a greenhouse environment.
*Duration of flowers*.—6 days.
*Corolla texture*.—Smooth.
*Shape*.—Funnel form.
*Lobing of the flower*.—Weak.
*Fragrance*.—Absent.
*Flowers per plant*.—50.
*Flower depth*.—2.5 cm.
*Flower tube length*.—0.8 cm.
*Flower tube diameter*.—3.8 cm.
*Flower throat diameter*.—0.6 cm.
*Pedicel color*.—RHS 144B (Yellow-Green).
*Pedicel length*.—0.9 cm to 1.8 cm.

Flower bud:
*Surface texture*.—Smooth, pubescent on the petal ribs.
*Typical number of buds per plant*.—10.
*Length*.—1.8 cm.
*Diameter*.—0.5 cm.
*Shape*.—Irregular.
*Color*.—The throat is RHS 1C (Green-Yellow) and the limbs are RHS 166B (Greyed-Orange).

Peduncles:
*Length*.—0.9 cm to 1.8 cm.
*Diameter*.—0.1 cm.
*Color*.—RHS 144B (Yellow-Green).
*Texture*.—Puberulent.
*Anthocyanin color*.—Absent.

Sepals:
*Calyx*.—Funnel shaped, salver-form.
*Shape*.—Lanceolate.
*Surface texture* (*both upper and lower surfaces*).—Densely glandular pubescence.
*Quantity per flower*.—5.
*Apex*.—Narrowly acute.
*Margin*.—Ciliate.
*Length*.—1.5 cm.
*Diameter*.—0.35 cm.
*Sepal color*.—Upper surface: RHS 137B (Green). Lower surface: RHS 137C (Green).

Petals:
*Shape*.—Obcordate.
*Quantity per flower*.—5 petals/lobes.
*Length*.—1.85 cm.
*Apex*.—Emarginate.
*Margin*.—Entire.
*Base*.—Fused in the tube.
*Texture, upper surface*.—Glabrous.
*Texture, lower surface*.—Smooth but dense along venation.
*Lobe length*.—0.8 cm.
*Lobe width*.—1.7 cm.
*Color*.—Lobe color: Upper surface: RHS 35A (Orange-Red) with RHS 30C (Orange-Red) veins and fading to RHS 26A (Orange) with RHS 47B (veins). Lower surface: RHS 180D (Greyed-Red) with RHS N186C (Greyed-Purple) veins and fading to RHS N34A (Orange-Red) with RHS 183B (Greyed-Purple) veins. Color of transition from petal/lobe to corolla tube (upper surface): RHS 34A (Orange-Red) and fading to RHS 47B (Red); transition lobe color size is small and star-shaped. Corolla tube color: Inner surface: RHS 2A (Yellow) with RHS 187A (Greyed-Purple) veins. Outer: RHS 1C (Yellow) with RHS N186C (Greyed-Purple).
*Fragrance*.—Absent.

Reproductive organs:
*Stamen number*.—5.
*Anther color*.—RHS 8A (Yellow).
*Anther shape*.—Bi-lobed, and ovoid.
*Anther length*.—0.1 cm.
*Filament color*.—RHS 154C (Yellow-Green).
*Filament length*.—0.9 cm to 1.2 cm.
*Pollen color*.—RHS 8B (Yellow).
*Pollen amount*.—Abundant.
*Placenta arrangement*.—Ovate.
*Pistil number*.—1.
*Pistil length*.—0.8 cm.
*Stigma color*.—RHS 139A (Green).
*Stigma shape*.—Funnel.
*Style length*.—0.75 cm.
*Style color*.—RHS 150B (Yellow-Green).

Fruit and seed set: No fruit or seed set observed.

COMPARISON OF 'KLECA19545' WITH PARENTAL LINES AND KNOWN VARIETY

'KLECA19545' is distinguished from the parental lines as follows. While 'KLECA19545' has orange-reddish colored petals, both the female parent, 'CA-2015-6388' and the male parent, 'KLECA17003', have yellow colored petals.

'KLECA19545' can be compared to the commercial *Calibrachoa* variety 'KLECA17328' (U.S. Plant application Ser. No. 16/350,101) as follows. 'KLECA19545' has very early flowering, strong vigor and weak conspicuousness of the veins, while 'KLECA17328' has early flowering, medium vigor, and no conspicuousness of the veins.

I claim:

1. A new and distinct variety of *Calibrachoa* plant designated 'KLECA19545' as illustrated and described herein.

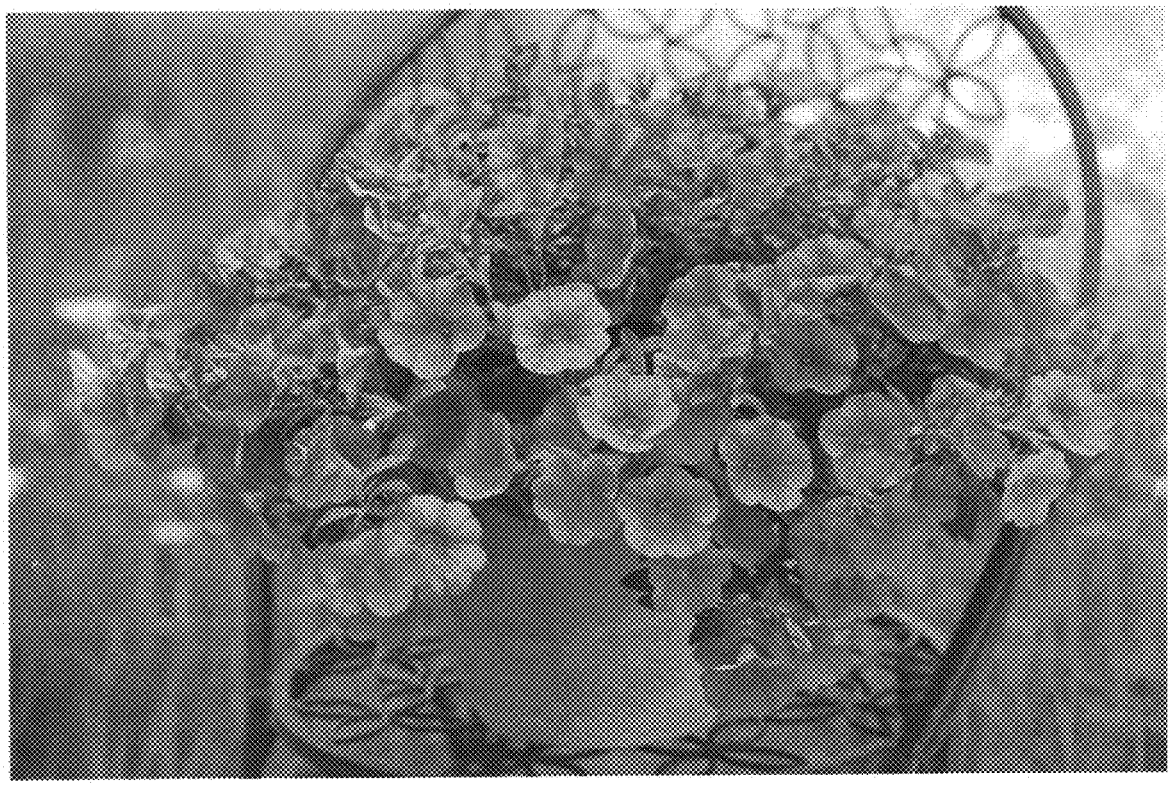

* * * * *